United States Patent
Kroll et al.

(10) Patent No.: US 8,123,716 B1
(45) Date of Patent: Feb. 28, 2012

(54) PERICARDIAL DELIVERY OF TREATMENT

(75) Inventors: Mark W. Kroll, Crystal Bay, MN (US); Yougandh Chitre, Valencia, CA (US)

(73) Assignee: Pacesetter, Inc., Sylmar, CA (US)

(*) Notice: Subject to any disclaimer, the term of this patent is extended or adjusted under 35 U.S.C. 154(b) by 570 days.

(21) Appl. No.: 11/768,793

(22) Filed: Jun. 26, 2007

(51) Int. Cl.
- A61M 31/00 (2006.01)
- A61M 25/00 (2006.01)
- A61M 37/00 (2006.01)
- A61N 1/30 (2006.01)
- A61N 1/00 (2006.01)
- A61K 9/22 (2006.01)

(52) U.S. Cl. .......... 604/65; 604/20; 604/21; 604/264; 604/66; 604/67; 604/523; 604/82; 604/890.1; 604/891.1; 604/92; 607/2; 607/3

(58) Field of Classification Search .......... 604/65, 604/66, 67, 82, 890.1, 891.1, 92, 93.01, 20, 604/21, 264, 523; 607/2, 3
See application file for complete search history.

(56) References Cited

U.S. PATENT DOCUMENTS

| | | | | |
|---|---|---|---|---|
| 4,506,680 | A * | 3/1985 | Stokes | 607/120 |
| 5,417,717 | A * | 5/1995 | Salo et al. | 607/18 |
| 5,797,870 | A * | 8/1998 | March et al. | 604/506 |
| 5,938,654 | A * | 8/1999 | Wong et al. | 604/892.1 |
| 6,179,809 | B1 * | 1/2001 | Khairkhahan et al. | 604/95.04 |
| 6,206,914 | B1 | 3/2001 | Soykan et al. | |
| 6,254,573 | B1 * | 7/2001 | Haim et al. | 604/157 |
| 6,374,876 | B2 * | 4/2002 | Bynum | 141/330 |
| 6,468,263 | B1 * | 10/2002 | Fischell et al. | 604/890.1 |
| 6,571,125 | B2 * | 5/2003 | Thompson | 604/20 |
| 6,824,561 | B2 | 11/2004 | Soykan et al. | |
| 2003/0032998 | A1 * | 2/2003 | Altman | 607/120 |
| 2003/0153951 | A1 * | 8/2003 | Ideker et al. | 607/3 |
| 2005/0143802 | A1 | 6/2005 | Soykan et al. | |
| 2005/0154370 | A1 * | 7/2005 | Sigg et al. | 604/503 |
| 2005/0165466 | A1 * | 7/2005 | Morris et al. | 607/116 |

FOREIGN PATENT DOCUMENTS

| | | |
|---|---|---|
| EP | 1015017 B1 | 3/2004 |
| EP | 1426021 A1 | 6/2004 |
| WO | 9955360 | 11/1999 |
| WO | 0012028 | 3/2000 |

* cited by examiner

*Primary Examiner* — Bhisma Mehta
*Assistant Examiner* — Shefali Patel

(57) ABSTRACT

An implantable cardiac therapeutic device having at least one implantable sensor arranged to sense at least one physiologic characteristic of a patient, an implantable therapeutic agent delivery assembly wherein the delivery assembly and a therapeutic agent to be delivered are configured for placement in a patient's pericardial space, and a controller in communication with the at least one implantable sensor and with the therapeutic agent delivery assembly wherein the controller evaluates the at least one physiologic characteristic for indications of a condition indicating administration of the therapeutic agent and wherein, upon detection of such indications, induces the therapeutic agent delivery assembly to deliver the agent. Also an implantable patient lead adapted for connection to a separable implantable therapy device, the lead including an implantable therapeutic agent delivery assembly wherein the delivery assembly and a therapeutic agent to be delivered are configured for placement in a patient's pericardial space.

22 Claims, 6 Drawing Sheets

PERICARDIAL DELIVERY OF TREATMENT

FIELD OF THE INVENTION

The invention relates to the field of treatment of acute medical conditions, such as myocardial ischemia, and to delivery of therapeutic compositions to a pericardial delivery site via an implantable device.

BACKGROUND OF THE INVENTION

Ischemia refers to a localized anemia, such as an acute condition arising from blockage in arteries supplying the affected tissue. Infarction refers to necrosis of tissue resulting from a failure in the blood supply. Myocardial infarction (MI) refers to infarction or necrosis of heart muscle tissue, frequently resulting from extended severe myocardial ischemia, such as due to occlusion of one or more coronary arteries. MI is a serious condition as the dead heart muscle results in permanent impairment and can even result in death.

If ischemia is detected before MI occurs, a variety of effective therapies and treatments are known. However, there exist several difficulties with early identification of ischemia and provision of appropriate therapies. One difficulty is that ischemic events are frequently of a silent nature, e.g., an ischemic event occurs without causing symptoms which are noticed by the afflicted person or without presenting obvious external indications. Further, ischemia can manifest as a chronic and progressive condition, such that a patient may undergo a number of ischemic episodes before becoming aware of the condition.

Once ischemia is detected, however, a number of therapies are available for effectively treating the condition and hopefully preventing progression to MI. For example, thrombolytic agents, such as tissue-type plasminogen activator (TPA), can be administered to dissolve and break-up blood clots which are a frequent cause of ischemia/MI. Angioplasty can also be performed to open blocked or occluded vessels. In the case of administration of thrombolytic agents, it has been generally shown that administration of these agents is beneficial if provided relatively rapidly (typically within three hours or less) of symptoms becoming apparent. Thus, for administration of thrombolytic agents to be most effective, the person experiencing the symptoms must usually be transported to a medical facility within a relatively brief period of time. Many thrombolytic agents are preferably delivered in a localized manner, further indicating administration by a physician. A further complication is that certain thrombolytic agents, including TPA, require controlled refrigeration to maintain their effectiveness, again indicating controlled storage and administration of such agents by clinical personnel.

A number of diagnosis techniques are known which can reveal ischemia indications, even if the ischemia has been of the silent type. For example, a surface electrocardiogram (ECG) utilizes a plurality of surface electrodes arranged in a well understood manner to monitor and evaluate a plurality of electrical vectors across the patient's body to reveal underlying physiologic activity. Ischemia typically exhibits characteristic changes in the electrophysiologic characteristics of the patient to provide indicators of the presence of ischemia. For example, characteristic changes typically occur in the ST segment, the T-wave, and/or the Q-wave. While surface ECGs are widely known and understood, they are typically limited to bedside or clinical use. Holter monitors or recorders can provide similar functionality in a portable unit to provide round the clock information without requiring continuous presence of the patient in a clinical setting. However, as external devices, Holter monitors are inconvenient to the patient and are not considered acceptable for long term continuous monitoring.

Thus it will be appreciated that there exists a need for a new system and method for early detection of ischemia, preferably before proceeding to MI. There is also a need for systems and methods not only for early detection of an ischemia condition, but also to facilitate prompt therapeutic intervention. There is a particular need for a system and method which is suitable for long term extended use by the patient, for example, in cases where ischemia may be chronic but intermittent, to provide long term monitoring without unduly inconveniencing the patient, such as via presence of an obtrusive external device. There is also a need for systems and methods to facilitate administration of time sensitive therapeutic agents, such as TPA, within the effective time window and free from the requirement that the patient be present in a clinical setting.

SUMMARY OF THE INVENTION

Embodiments of the invention provide an implantable device to provide the ability for long term extended monitoring of the patient's condition without presenting the inconveniences of an external device. As noted above, surface-based ECG measurements are a well known and understood clinical tool for evaluating a patient's condition, including the presence of ischemia. In certain embodiments, an implantable device is provided with one or more physiologic sensors configured to be implanted within the patient to also sense physiologic-based signals which can be characterized as indicative of ischemia. In one embodiment, one or more electrodes are arranged to sense the patient's cardiac activity for indications of ischemia.

In certain aspects, the invention also provides a system for localized delivery of therapeutic agents to cardiac tissue upon observations of indications for delivery of the therapeutic agent. In certain embodiments, therapeutic agents are delivered as indicated to a pericardial space to more effectively deliver the therapeutic agent to the affected tissue, as well as to avoid the complications of intravenous/intra-arterial delivery. The therapeutic agents are provided in a form that does not require refrigeration, thereby facilitating implanted positioning of the agents, and also such that the agent can be very rapidly administered upon indications therefore. In certain embodiments, a therapeutic agent delivery system is combined with a cardiac rhythm management system such that pacing, shocking, and/or drug administration therapies can be combined and provided as indicated to provide a broader range of therapies available directly to the patient.

By providing these therapies in an implantable device, the need for the patient to be present in a clinical setting for receipt of the therapy is significantly reduced. A further advantage of certain embodiments is that by employing implantable physiologic sensors which can be arranged more proximal the affected patient tissue of interest, embodiments of the invention can provide increased sensitivity to facilitate early detection of possible milder ischemic events. This would be more difficult to detect with surface ECG-based systems employing surface sensors arranged more distally from the affected tissue of interest and with the relatively high impedance of the patient's skin interposed therebetween. Further advantages are that certain embodiments perform evaluation of sensed signals for indicators of ischemia on an automated basis, thus reducing the need for a highly skilled and trained clinician to interpret sensed data.

One embodiment includes an implantable cardiac therapeutic device comprising at least one implantable sensor arranged to sense at least one physiologic characteristic of a patient, an implantable therapeutic agent delivery assembly wherein the delivery assembly and a therapeutic agent to be delivered are configured for at least partial placement in a patient's pericardial space, and a controller in communication with the at least one implantable sensor and with the therapeutic agent delivery assembly wherein the controller evaluates the at least one physiologic characteristic for indications of a condition indicating administration of the therapeutic agent and wherein, upon detection of such indications, induces the therapeutic agent delivery assembly to deliver the agent.

Another embodiment includes an implantable patient lead adapted for connection to a separable implantable therapy device, the lead comprising an implantable therapeutic agent delivery assembly wherein the delivery assembly and a therapeutic agent to be delivered are configured for placement at least partially in a patient's pericardial space.

A further embodiment includes a method of treating myocardial ischemia, the method comprising implanting at least one releasable dose of thrombolytic agent adjacent a patient's heart, implanting at least one physiologic sensor, automatically monitoring activity sensed by the at least one implanted physiologic sensor for indications of myocardial ischemia, and upon observation of indications of myocardial ischemia, inducing the release of at least one dose of the thrombolytic agent. These and other objects and advantages of the invention will become more apparent from the following description taken in conjunction with the accompanying drawings.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
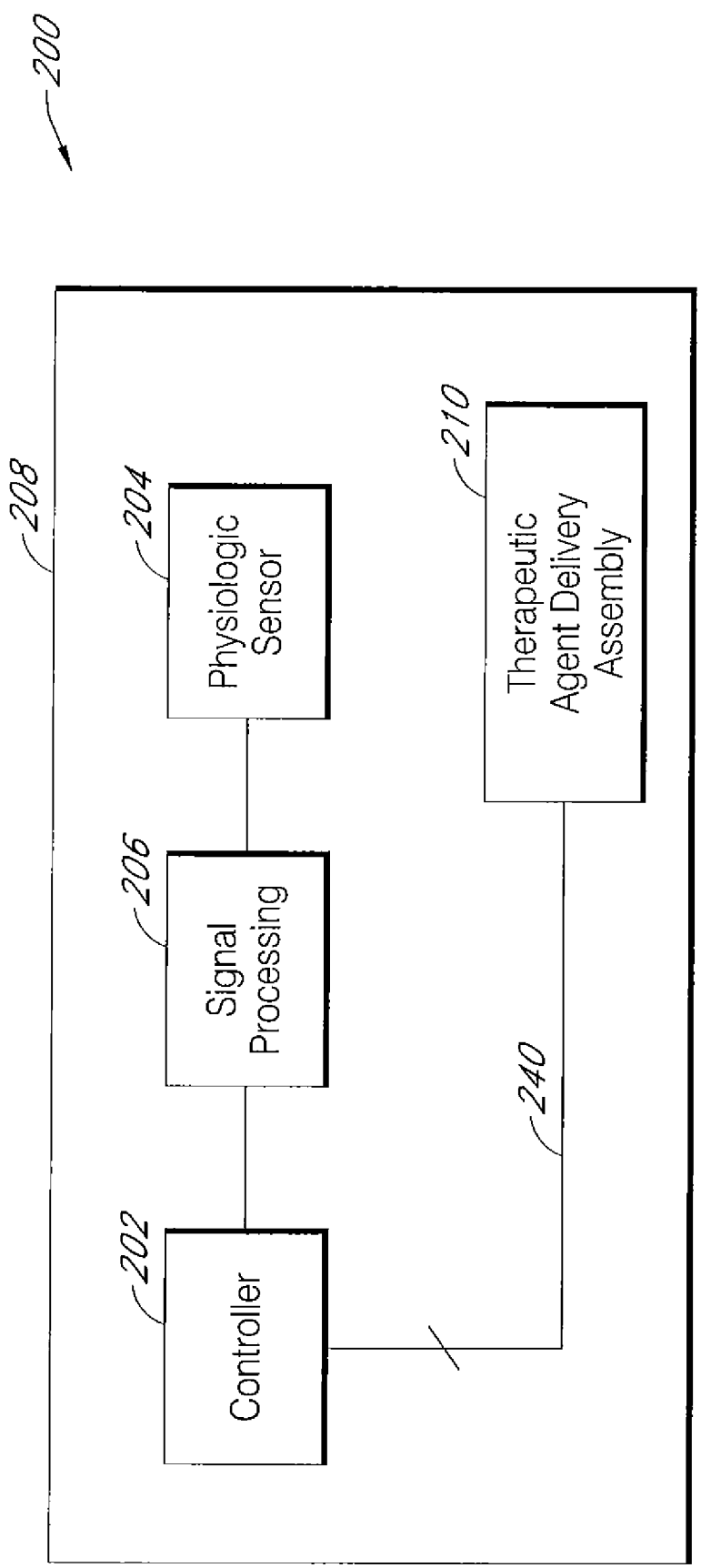
FIG. 1 is a high level functional block diagram of one embodiment of a system for pericardial treatment of myocardial ischemia.

FIG. 1 illustrates a high level functional block diagram of one embodiment of a system for pericardial treatment of myocardial ischemia 200, referred to hereafter as the system 200 for brevity. The system 200 is configured for extended long-term implantation to provide ongoing monitoring of the patient's condition, which in certain embodiments includes for indications of ischemia. The system 200 is further configured to automatically evaluate sensed physiologic conditions and to evaluate these conditions without requiring direct intervention of a physician or other trained clinical personnel. The system 200 is further configured in certain embodiments, upon detection of ischemia indicators, to automatically deliver appropriate therapy which can include administration of therapeutic agents also without requiring the direct intervention of a physician or other clinical personnel. Certain embodiments of the system 200 are configured to extend at least partially within the pericardial space.

In one embodiment, the system 200 includes a controller 202 adapted to perform the control and management functions of the system 200. The controller 202, in certain embodiments, is microprocessor-based and includes associated memory and storage devices, for example, to store control programs and data. In this embodiment, the system 200 also includes one or more physiologic sensors 204. The physiologic sensors 204 are configured for implantation so as to perform extended long-term sensing of one or more physiologic parameters of the patient. In certain embodiments, the one or more physiologic sensors 204 include electrode structures which can be arranged adjacent or in contact with the patient's cardiac tissue to thereby sense the patient's cardiac activity. In one embodiment, at least one of the physiologic sensors 204 is configured for implantation within a patient's pericardial space.

In one embodiment, the system 200 also includes a signal processing module 206 providing an interface between the one or more physiologic sensors 204 and the controller 202. In this embodiment, the signal processing module 206 provides appropriate filtering, signal amplification, and analog/digital conversion to thereby provide signals to the controller 202 indicative of the physiologic activity sensed by the one or more physiologic sensors 204.

In this embodiment, the system 200 also comprises a therapeutic agent delivery assembly 210. The therapeutic agent delivery assembly 210 is configured to communicate with the controller 202 to be thereby provided with appropriate control/power signals 240. Upon appropriate command from the controller 202, the therapeutic agent delivery assembly 210 is further configured to release or administer a determined dose of therapeutic agent to target tissue.

In certain embodiments, the therapeutic agent delivery assembly 210 is further configured for implantation substantially within the patient's pericardial space for more localized delivery to tissue which may be affected by ischemia. In certain embodiments, the therapeutic agent delivery assembly 210 is provided as separate components and/or to have separate delivery avenues such that therapeutic agent can be delivered to a plurality of target sites of the patient's heart. In certain embodiments, first components of the therapeutic agent delivery assembly 210 are configured for implantation inside the patient's pericardial space and remainder second components of the therapeutic agent delivery assembly 210 are configured for implantation outside the patient's pericardial space.

In one embodiment, the system 200 further comprises a biocompatible enclosure 208 which encloses the controller 202, the one or more physiologic sensors 204, the signal processing module 206, and the therapeutic agent delivery assembly 210. The biocompatible enclosure 208 is formed of biocompatible material and configured with an outer contour to reduce irritation and damage when implanted. In certain embodiments, the biocompatible enclosure 208 is configured such that only a portion of the system 200 is configured to be implanted within the patient's pericardial space. For example, in one embodiment, one or more physiologic sensors 204 and the therapeutic agent delivery assembly 210 are configured for placement within the patient's pericardial space with the controller 202, signal processing module 206, and possibly other components of the system 200 configured to be implanted at a location outside of the patient's pericardial space.

Figure 2:
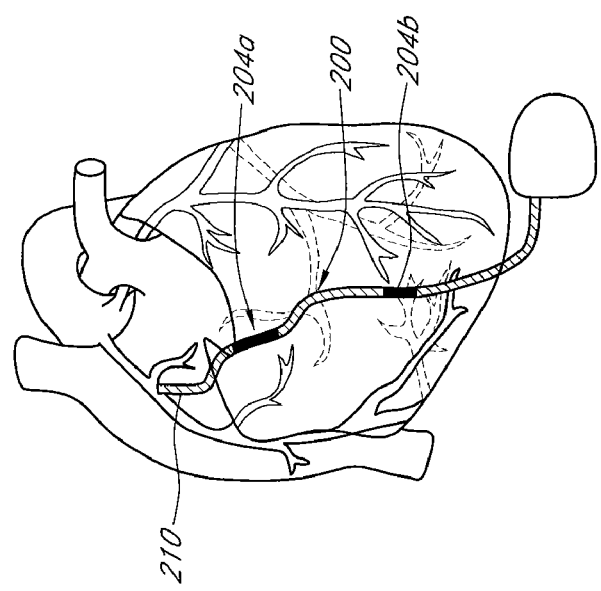
FIG. 2 is a schematic illustration of a patient's heart and further provided with one embodiment of a system for pericardial treatment of myocardial ischemia.

FIG. 2 illustrates schematically a patient's heart, the patient being provided with one embodiment of the device 200. In this embodiment, the device 200 includes two physiologic sensors 204a, 204b, with both sensors 204a, 204b being configured for implantation within the patient's pericardial space. In this embodiment, the device 200 further comprises a therapeutic agent delivery assembly 210 which, in this embodiment, is arranged at an end of the device 200 and further configured for positioning adjacent the patient's right atria. In other embodiments, a preferred location for a therapeutic agent delivery assembly 210 is over or adjacent the left main coronary artery. In these embodiments, therapeutic agent can be delivered adjacent both the left anterior descending artery (LAD) and left circumflex (LCX). In these embodiments, therapeutic agent is delivered as indicated substantially directly to the myocardium, thereby significantly reducing adverse effects of MI and/or stroke and reducing the likelihood for permanent disability.

Figure 3:
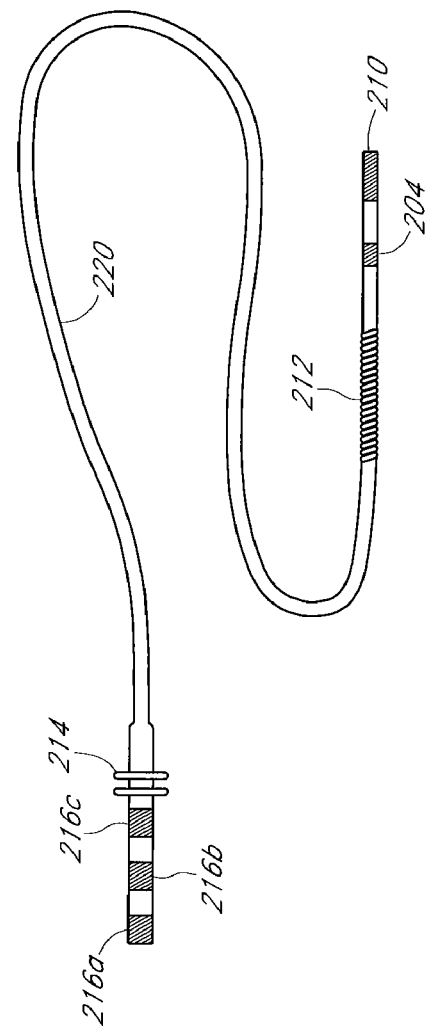
FIG. 3 illustrates one embodiment of an implantable patient lead, including at least physiologic sensor and a therapeutic agent delivery assembly.

FIG. 3 illustrates one embodiment of a portion of the system 200 comprising an implantable patient lead 220. The implantable patient lead 220 is configured for implantation within a patient for sensing of signals corresponding to physiologic activity/status as well as for delivery of therapy as indicated. In this embodiment, the implantable patient lead 220 is at least partially formed with exterior materials of a biocompatible nature. The implantable patient lead 220 is at least partially flexible to accommodate curves or bending for example during the implantation process as well as extending in situ in a partially curved manner.

In this embodiment, the implantable patient lead 220 comprises at least one physiologic sensor 204 and therapeutic agent delivery assembly 210. In one embodiment, the physiologic sensor 204 is configured as a generally annular or ring-shaped electrode adapted to sense electrical signals corresponding to the patient's cardiac activity. The therapeutic agent delivery assembly 210 is configured to dispense therapeutic agent upon detection by the system 200 of conditions indicating administration of the therapeutic agent. In this embodiment, the therapeutic agent delivery assembly 210 is arranged at an end of the implantable patient lead 220, however, in other embodiments, a therapeutic agent delivery assembly 210 can be arranged proximal an end of the patient lead 220, however, not extending fully to the end of the patient lead 220 and in other embodiments, can be arranged at a more intermediate or medial position, depending upon the indications of a particular application. In this embodiment, the physiologic sensor 204 is arranged proximal the end of the implantable patient lead 220, however, positioned a distance away from the end of the lead 220, occupied in this embodiment by the therapeutic agent delivery assembly 210.

In this embodiment, the implantable patient lead 220 also comprises a stimulation electrode 212. The stimulation electrode 212 is configured generally as a coil, thereby defining a larger surface area, for example, for improved delivery of high energy shock stimulations. It will be understood that the configuration and dimensions of the stimulation electrode 212 can be readily adapted to the requirements of a specific application by one of ordinary skill. It will be further understood that this is simply exemplary of one embodiment and that in other embodiments of implantable patient leads 220, a subset of these components, additional components, or a revision in their relative positions can be implemented to satisfy the needs of particular applications.

In this embodiment, the implantable patient lead 220 further comprises a sealing structure 214. In this embodiment, the sealing structure 214 at least partially comprises biocompatible materials and further comprises materials having a resilient quality. The sealing structure 214 is further configured to engage with other components of the system 200 to provide a hermetic seal therebetween. In this embodiment, the implantable patient lead 220 further comprises one or more contacts 216. In one exemplary implementation, the implantable patient lead 220 comprises three contacts 216a, 216b, and 216c electrically isolated from each other via interposed dielectric material. The one or more contacts 216 are configured to establish an electrical connection with other components of the system 200, for example, with signal processing components 206. The contacts 216 are also in electrical contact with one or more distal components of the implantable patient lead 220, such as one or more therapeutic agent delivery assemblies 210, one or more physiologic sensors 204, and/or one or more stimulation electrodes 212.

This connection between the one or more contacts 216 and one or more corresponding distally positioned functional components of the lead 220 would typically be provided by insulated conductors extending in the interior of the patient lead 220, however, which are obscured from view in FIG. 3. Thus, in one embodiment, an implantable patient lead 220 is configured to extend at least partially within a patient's pericardial space, for example, to include at least one therapeutic agent delivery assembly 210. The implantable patient lead 220 is further configured to engage with other components of the system 200 which can be enclosed in a separate housing and include, for example, a controller 202 and signal processing 206. Thus, the system 200 can be configured such that a portion including at least one therapeutic agent delivery assembly 210 is arranged within the pericardial space with the remainder of the system 200 configured for implantation outside of the patient's pericardial space.

Figure 4:
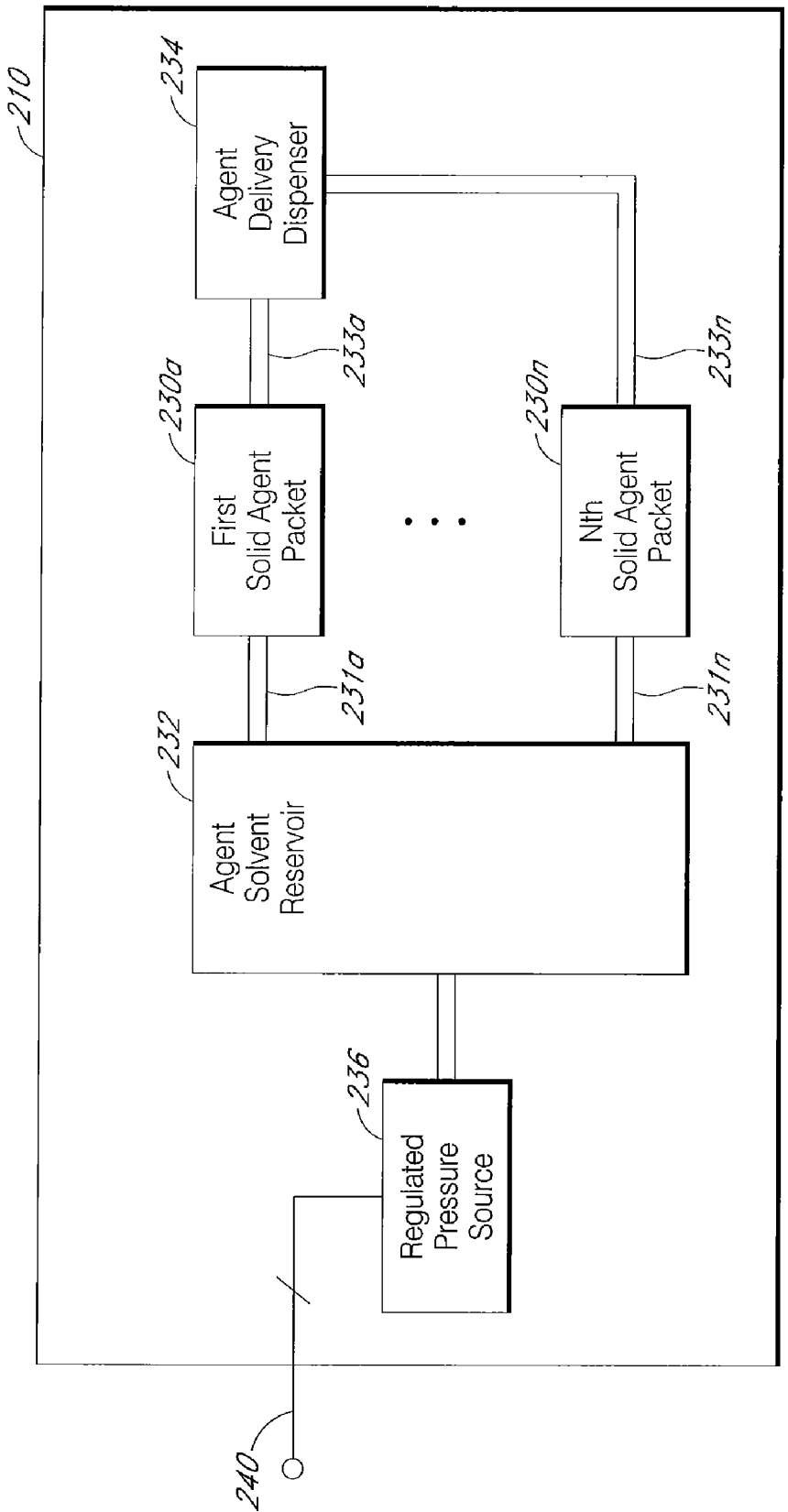
FIG. 4 is a more detailed functional block diagram of one embodiment of a therapeutic agent delivery assembly configured for implantation in a patient's pericardial space.

FIG. 4 illustrates in greater detail a functional block diagram of one embodiment of a therapeutic agent delivery system 210. In this embodiment, the therapeutic agent delivery assembly 210 is configured for implantation so as to extend at least partially in the patient's pericardial space and also configured to store a therapeutic agent and deliver one or more doses of the therapeutic agent as indicated.

In one embodiment, the assembly 210 comprises at least a first solid agent packet 230. In certain embodiments, the assembly 210 comprises a plurality of solid agent packets 230a-230n. The solid agent packet 230 holds a determined quantity of a therapeutic agent provided in solid form. In certain preferred embodiments, the solid agent is provided in a powdered form in the solid agent packet 230. For treatment of ischemia, the solid agent comprises a thrombolytic agent such as reteplase and/or alteplase.

In certain embodiments, the assembly 210 comprises a plurality of solid agent packets 230a-230n and further such that different determined quantities or doses of the agent are provided in a respective solid agent packet 230. In other embodiments, a plurality of solid agent packets 230a-230n are provided wherein different therapeutic agents are provided for a given solid agent packet 230. Thus, a first solid agent packet 230a contains a first type of therapeutic agent in solid form and a second solid agent packet 230b comprises a second type of therapeutic agent in solid form. These aspects provide the ability for certain embodiments of the assembly 210 to provide different doses of therapeutic agent and/or to provide different types of therapeutic agent.

In one embodiment, the assembly 210 further comprises one or more agent solvent reservoirs 232. The one or more agent solvent reservoirs contain an appropriate solvent for associated one or more solid agent packets 230. The one or more agent solvent reservoirs 232 are connected to an associated solid agent packet 230 via a corresponding conduit 231. The assembly 210 is further configured such that agent solvent contained in the agent solvent reservoir 232 can be conveyed via the corresponding conduit 231 to the respective solid agent packet 230 to allow the solvent to dissolve the solid agent and form a solution of the therapeutic agent. It will be understood that the composition of the solvent is selected to provide relatively rapid formation of a solution when combined with the solid agent and the composition of an appropriate solvent, as well as any other additions thereto will be well understood by one of ordinary skill for the needs of a particular application.

The assembly 210 further comprises at least one agent delivery dispenser 234 which is configured to deliver the agent solution formed by a combination of the solid agent and the agent solvent for delivery or administration to the target patient tissue. In one embodiment, one or more corresponding conduits 233a-233n connect the agent delivery dispenser 234 with associated one or more solid agent packets 230a-230n. In certain embodiments, the agent delivery dispenser 234 is configured not only for delivery or administration of therapeutic agent, but can also perform a securing or fixation function as described in greater detail below.

In one embodiment, the assembly 210 further comprises one or more pressure sources 236. The pressure source 236 provides pressure to the agent solvent reservoir 232 such that the assembly 210 can selectively induce solvent from the reservoir 232 to move into contact with the solid agent to thereby facilitate formation of a solution of the therapeutic agent as well as administration of the agent to the target tissue. In various embodiments, the pressure source 236 can comprises a resilient bladder-type structure applying compressive pressure to the agent solvent reservoir 232 to facilitate inducement of the solvent into contact with the solid agent. In other embodiments, the pressure source 236 comprises a pump to induce the solvent into contact with the solid agent.

Thus, in certain embodiments, the assembly 210 comprises a two-stage pump wherein a first stage induces a liquid solvent into contact with a solid agent to thereby form a solution for delivery via a second stage of the pump, such as via the agent delivery dispenser 234. In certain embodiments, it is preferred that the pressure source 236, be regulated to thereby control formation of a therapeutic agent solution and delivery of the same to target patient tissue. In various embodiments, this regulation of delivery of agent by the assembly 210 can be provided by appropriate valving, for example, between the reservoir 232 and corresponding one or more solid agent packets 230a-230n. In other embodiments, regulation can be provided directly via regulation of the pressure source 236 and further via non-active valving, for example, impermeable rupturable membranes arranged between one or more solvent reservoirs 232 and corresponding solid agent packets 230. In one embodiment, regulation or control of delivery of the therapeutic agent solution is provided by one or more control/power signals 240, such as provided by the controller 202 (see FIG. 1). The number and characteristics of the control/power signals 240 will be readily understood by one of ordinary skill based on the requirements of a particular application, for example, including whether or not the pressure source 236 is powered, as well as a number and configuration of the solid agent packets 230.

Figure 5:
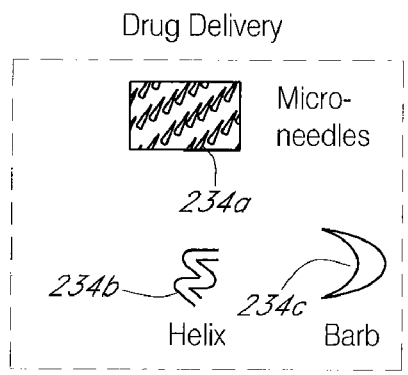
FIG. 5 illustrates several embodiments of agent delivery dispensers configured for administration of a therapeutic agent adjacent target patient tissue, in one embodiment within the pericardial space.

FIG. 5 illustrates exemplary embodiments of agent delivery dispensers 234. In one embodiment, an agent delivery dispenser 234a is configured generally as an array of microneedles configured for engagement with target tissue. In another embodiment, an agent delivery dispenser 234b is configured generally as a helix having a passage therein for delivery of therapeutic agent solution. In a further embodiment, an agent delivery dispenser 234c is configured generally as a barb or hook also having an internal passage for delivery of therapeutic agent. Thus, in certain embodiments, one or more agent delivery dispensers 234 can be configured not only for delivery of therapeutic agent, but are also configured to be manipulated to hook into, screw into, or otherwise secure to patient tissue. Thus, the agent delivery dispenser 234 can provide the function not only of delivering therapeutic agent to target tissue, but also act to secure or fixate the therapeutic agent delivery assembly 210 in a desired location via cooperative engagement with patient tissue. It will thus be understood that in certain embodiments, the agent delivery dispenser 234 is preferably formed of biocompatible material and further configured to accommodate additional tissue growth which may occur following fixation of the assembly 210 in a desired position.

Figure 6:
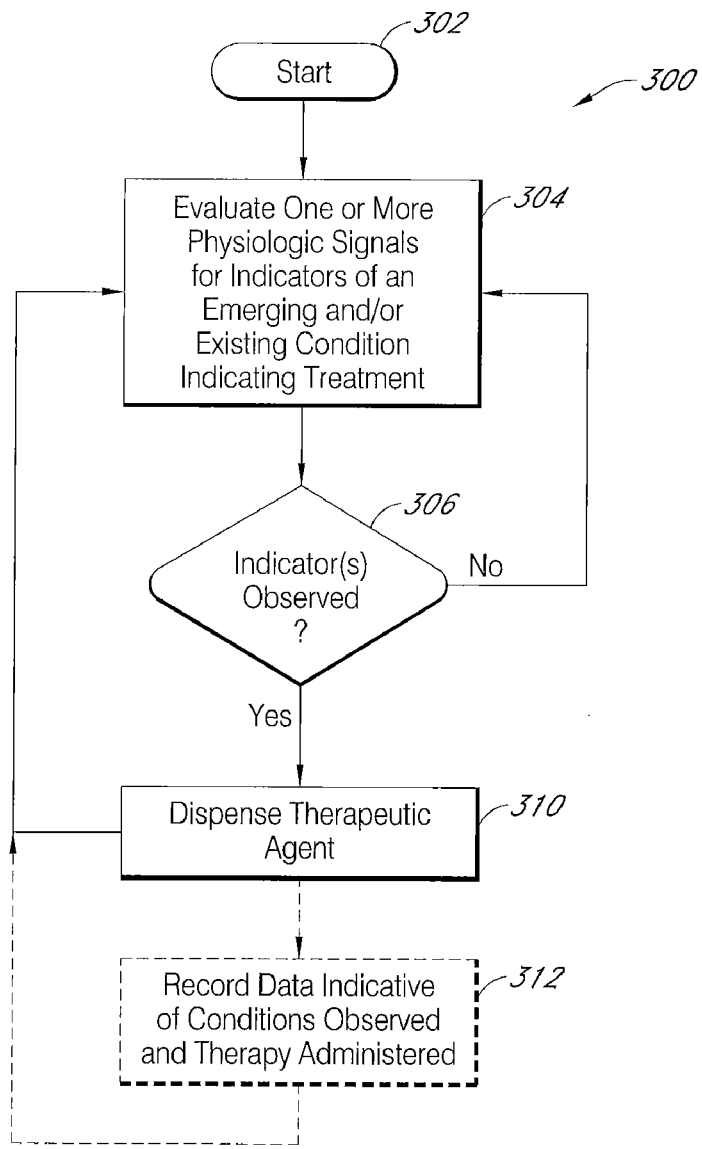
FIG. 6 is a flow chart of one embodiment of a method of pericardial treatment of myocardial ischemia.

FIG. 6 illustrates a flow chart of one embodiment of a method 300 of pericardial treatment of myocardial ischemia. In certain embodiments, the method 300 includes the delivery of therapeutic agent as indicated and in certain embodiments, can also include the selective delivery of other therapies, such as cardiac rhythm management therapy. The method 300 begins in a start block 302. The start block 302 generally includes implantation and individual adjustment/programming of a system. In one embodiment, the system is adapted for pericardial treatment of myocardial ischemia, such as can be provided by the system 200 previously described. As previously noted, in certain embodiments, the method 300 also includes other observation and therapy generation and delivery, such as electrical stimulation, which may proceed in parallel with other processes of an implantable device. The following description will focus on indications and delivery of therapeutic agents for ease of understanding of certain aspects of the invention.

Following from the start block 302 is a block 304 wherein one or more physiologic signals are evaluated for indications of an emerging and/or existing conditions indicating treatment. In certain embodiments, the system 200 includes one or more physiologic sensors 204 configured to sense electrical signals corresponding to the patient's cardiac activity. This can be utilized in certain embodiments to evaluate for depression or elevation in an ST segment and/or T-wave distortions of the patient's IEGM. In other embodiments, an IEGM signal can be analyzed for appearance of characteristic notches in the QRS complex or other unusual transitional signals, sometimes referred to as fragmentation. In certain embodiments, time-based measurements of the patient's physiologic activity are converted into the frequency domain and the frequency characteristics of the physiologic activity are analyzed for indications of a condition indicating treatment, for example, ischemia. In certain embodiments, physiologic sensors 204 can be arranged spatially to define different spatial sensing vectors to localize anomalous conditions.

When the system 200 and method 300 are able to isolate localized conditions, in embodiments including multiple agent delivery sites, delivery of the therapeutic agent can be selected to be more adjacent the affected tissue. In other embodiments, a physiologic sensor 204 can be configured as a pressure sensor and/or to sense other parameters, such as $PO_2$, $PCO_2$, pH, and other physiologic, chemical, and/or physical parameters which can be analyzed for indications of an emerging and/or existing condition. A variety of algorithms and characteristic physiologic activity will be well understood by one of ordinary skill for evaluating indications of conditions including ischemia and can be readily implemented by one of ordinary skill without detracting from the scope of the invention.

Following from the evaluation of block 304 is a decision block 306 wherein a decision is made as to whether or not appropriate indicators have been observed to recommend administration of therapeutic agent. If the evaluation of block 306 is negative, the method proceeds with the evaluation of block 304 for possible subsequent emergence of appropriate indicators. If the decision of block 306 is affirmative, the method 300 proceeds to a block 310 wherein therapeutic agent is dispensed, in certain preferred embodiments, directly to myocardial tissue within the pericardial space.

As previously noted, in certain embodiments, the system 200 includes the ability to deliver different doses of therapeutic agent and/or to administer different types of therapeutic agent. Thus, in certain embodiments, block 310 includes not simply administration of therapeutic agent, but also administration of a determined dose of the agent and/or administration of a determined type of therapeutic agent. For example, the evaluation of block 304 can include determination of previously existing occurrences of indicators of therapy delivery and the method 300 can under such circumstances adjust the dose and/or type of therapeutic agent delivered to attempt to reduce the frequency and/or severity of recurrences of the condition.

In certain embodiments, the method 300 includes an optional block 312 wherein data indicative of conditions observed and therapy administered is recorded. For example, block 312 can record the particular physiologic activity which was observed indicating administration of therapeutic agent. Block 312 can be repeated for each instance of observation of indications of therapeutic agent delivery to provide trending data. For example, the recording of block 312 can provide the ability to track on an extended long-term basis the progression of a patient's condition. This aspect is particularly useful for paroxysmal conditions which may not reliably exhibit themselves during scheduled clinical examinations.

Block 312 also provides the ability to record history of administration of therapeutic agent(s). When combined with stored data indicative of the physiologic activity observed, block 312 can provide an automated recording indicative of the efficacy of the therapy administration, again on a long-term extended basis which would be inconvenient and expensive to provide in a clinical setting. The recording of block 312 can also provide valuable diagnostic data indicative of the efficacy of determined doses of therapeutic agent as well as the efficacy of the administration of different types of agent. This can provide valuable data to the clinician to further adjust and refine the patient's therapy.

Figure 7:
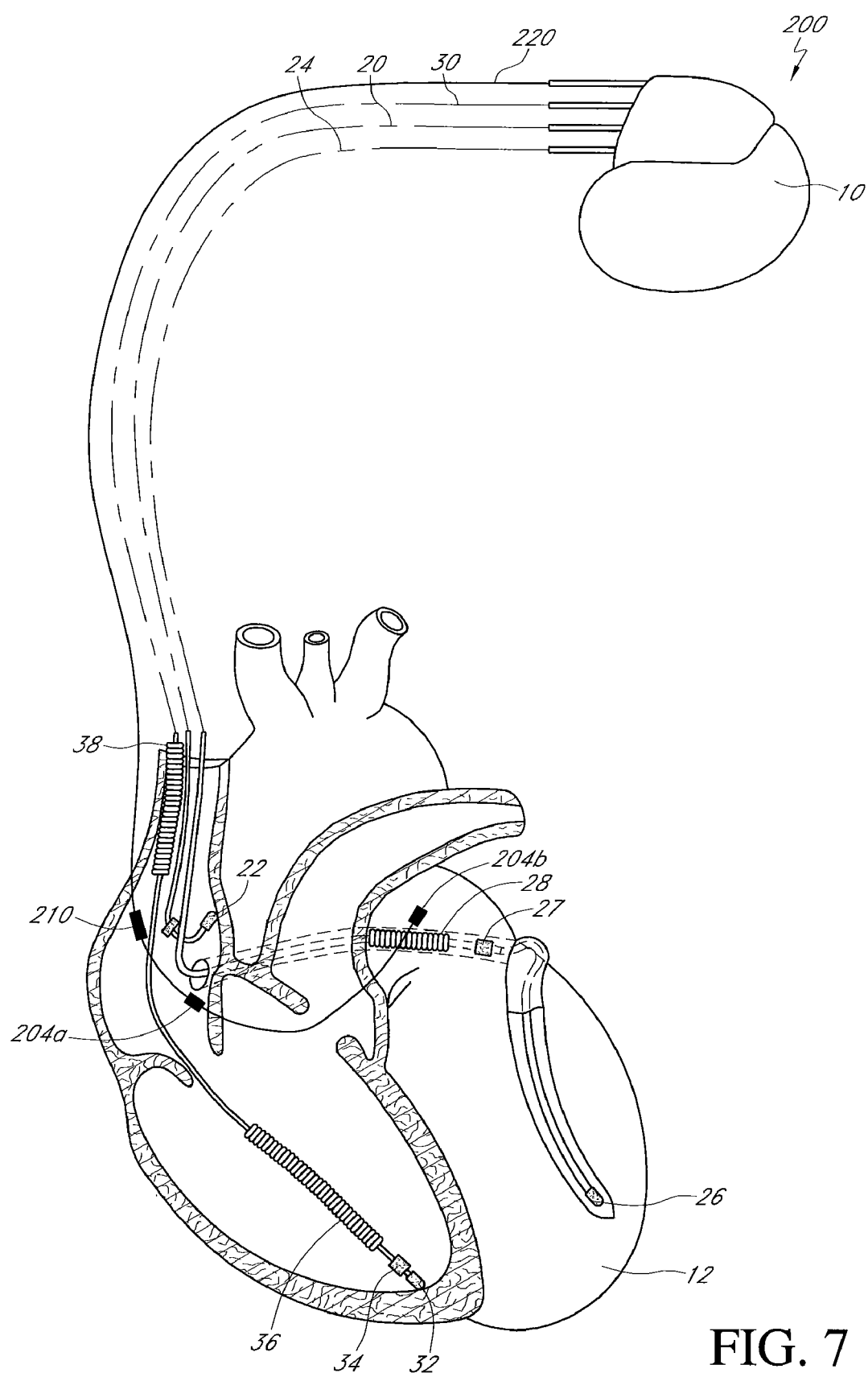
FIG. 7 is a simplified diagram illustrating an implantable stimulation device in electrical communication with at least three leads implanted into a patient's heart for delivering multi-chamber stimulation and shock therapy.

In one embodiment, as shown in FIG. 7, the system 200 comprises an implantable cardiac stimulation device 10 configured to establish electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As previously described, the system 200 is configured to be at least partially implanted pericardially. For example, in one embodiment, a patient lead 220 comprising sensors 204a and 204b and an agent delivery assembly 210 is configured for implantation within a desired pericardial space. In certain embodiments, the system 200 can be configured to be substantially or wholly implanted within a desired pericardial space.

Figure 8:
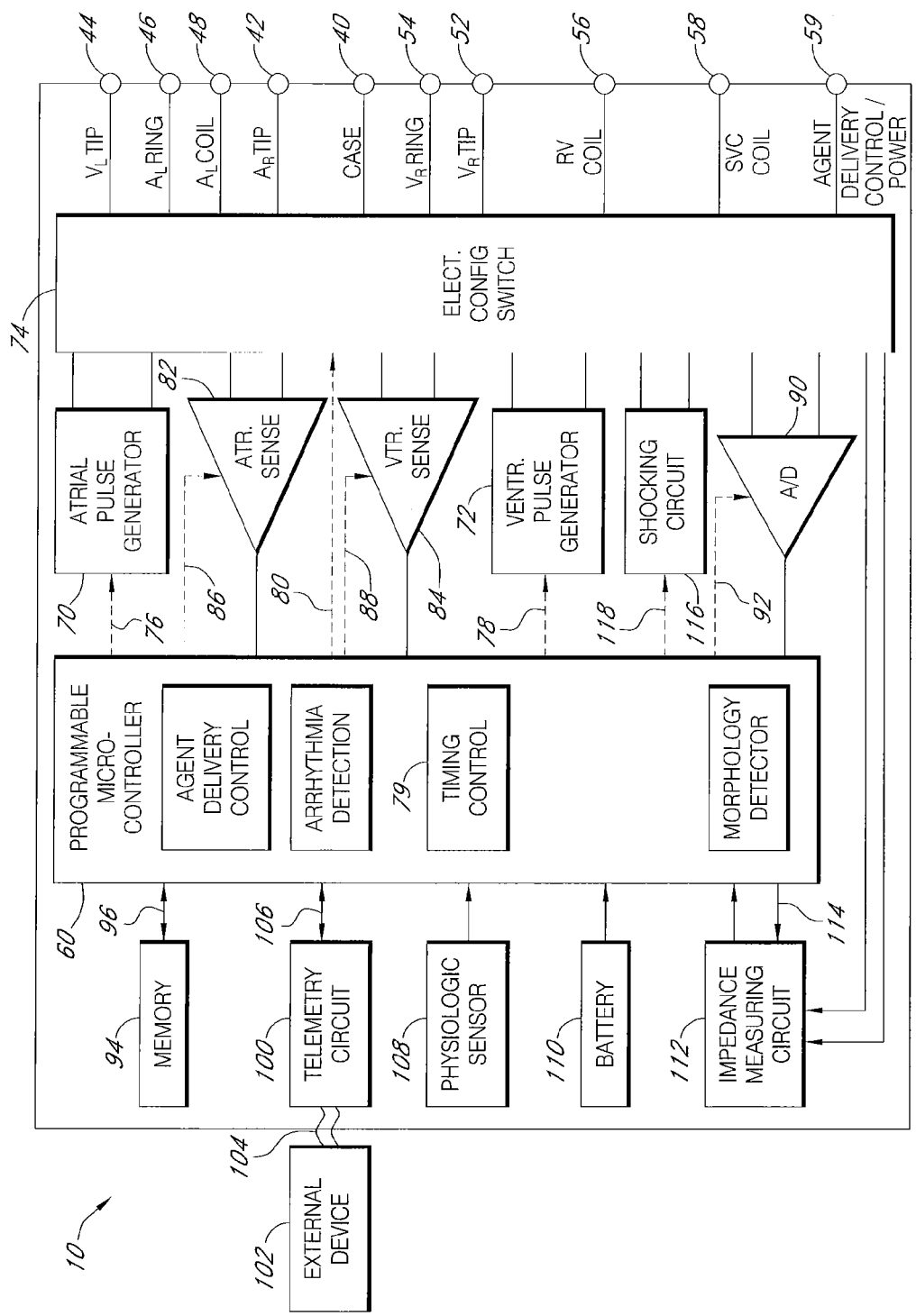
FIG. 8 is a functional block diagram of a multi-chamber implantable stimulation device illustrating the basic elements of a stimulation device which can provide cardioversion, defibrillation and pacing stimulation in four chambers of the heart.

As illustrated in FIG. 8, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 8, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, 58, and 59 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal (Rv COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. The terminal 59 is adapted to provide control signals to the therapeutic agent delivery assembly 210 as well as any needed power.

At the core of the stimulation device 10 is a programmable microcontroller 60 which controls the various modes of stimulation therapy and agent delivery. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 8, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller includes an agent delivery control that corresponds generally to the controller 202 and signal processing 206 described above with reference to FIG. 2. The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. Certain sensing functions of the device 10 indicate bandpass filtering capability in the range of approximately 20-40 Hz. In certain embodiments, for example embodiments directed to evaluation for depression and/or elevation in an ST segment and/or T-wave distortions, the capability of bandpass filtering in the range of approximately 1-10 Hz is preferred. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits receive control signals over signal lines 86, 88 from the microcontroller 60 for the purposes of controlling the gain, threshold, polarization charge removal circuitry (not shown), and the timing of any blocking circuitry (not shown) coupled to the inputs of the sensing circuits 82, 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals under control of a control signal 92 from the microcontroller 60, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 8. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 8, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Many patients have conditions which indicate that they be provided with a therapeutic cardiac therapy device. Embodiments of the invention are based at least in part on utilizing an implantable cardiac stimulation device, such as the device 10 previously described, for ongoing monitoring of the patient's condition. Certain embodiments utilize analysis based on sensing which is performed by the device 10 and can be utilized for other purposes, such as determining need for therapy delivery as previously described. Various embodiments are adapted for early detection of an emerging condition and to keep a record of data related to the emerging condition. These embodiments facilitate early detection of an emerging condition which may not manifest itself during a scheduled clinical evaluation. Certain embodiments also provide the ability to track or generate trend data, for example for monitoring for changes in a known or preexisting condition where the changes may indicate revision of a patient's therapy or other intervention.

Thus, various embodiments provide an implantable therapy device and methods of utilizing such a device to provide extended long-term evaluations of conditions indicative of administration of therapeutic agents. As in certain embodiments, implantable sensors are used, increased sensitivity is available which facilitates early detection of emerging conditions which may be of a relatively asymptomatic nature and presenting relatively minor observable characteristics as to complicate and render unlikely timely detection of the condition utilizing conventional diagnostic tools, such as surface ECGs.

Certain embodiments further provide therapeutic agents, such as thrombolytic agents including alteplase and reteplase in a solid form. In preferred embodiments, the solid agent is provided in a powdered form. A liquid solvent is selectively introduced to a dose of the solid powered agent to rapidly form a solution of the agent. The agent solution can be further induced for delivery to target tissue. In certain embodiments, the preferred delivery location is directly to myocardial tissue and at a delivery site within the pericardial space. The solid agent and corresponding solvent can be implanted with a delivery device in an implanted location, such as in the pericardial space to facilitate immediate availability of reconstituted agent solution. These aspects avoid the limitations of certain thrombolytic agents, such as TPA, which require refrigeration and are thus not suitable for storage and delivery in an implanted manner.

Embodiments of the invention also greatly simplify the implantation procedure by utilizing a sub-xiphoid approach for placement of one or more therapeutic agent delivery assemblies in a pericardial space, thereby avoiding the complications of intravenous/intraatrial delivery avenues. Certain embodiments also combine the ability to directly administer a therapeutic agent to target tissue with a variety of cardiac rhythm management therapies to provide a broader range of therapy availability for the patient. Embodiments also include the ability to record data indicative of conditions observed and therapy delivered to provide valuable trending and diagnostic data to a physician or other attending clinician.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac therapeutic device comprising:
   a lead configured for at least partial placement in a pericardial space;
   at least one implantable sensor on the lead and arranged to sense at least one physiologic characteristic of a patient;
   an implantable therapeutic agent delivery assembly entirely on the lead, the delivery assembly including a structure for holding a therapeutic agent for subsequent delivery, an agent delivery dispenser coupled to the structure by a conduit and configured to deliver the agent to a target tissue, and a pressure source configured to provide pressure to the structure to induce flow of the agent from the structure to the agent delivery dispenser, wherein at least a portion of the delivery assembly is configured for placement in the pericardial space and the agent is entirely contained within the structure that is entirely on the lead; and
   an implantable controller configured to be connected with the lead so as to be in electrical communication with the at least one implantable sensor and with the therapeutic agent delivery assembly wherein the controller evaluates the at least one physiologic characteristic for indications of a condition indicating administration of the therapeutic agent and wherein, upon detection of such indications, induces the therapeutic agent delivery assembly to deliver the agent.

2. The device of claim 1, wherein the structure for holding the therapeutic agent comprises an agent solvent reservoir configured to hold a liquid solvent, and a solid agent packet coupled to the reservoir by a second conduit and configured to hold a solid therapeutic agent, wherein the agent delivery dispenser is coupled to the solid agent packet.

3. The device of claim 2, wherein the solid therapeutic agent comprises a powdered form of the agent.

4. The device of claim 2, wherein the agent comprises one of reteplase and alteplase.

5. The device of claim 2, wherein the structure for holding the therapeutic agent comprises a plurality of packets of the solid therapeutic agent configured such that the device delivery assembly can deliver multiple doses of the agent.

6. The device of claim 5, wherein the plurality of packets are dimensioned such that the delivery assembly can deliver different dosages of the agent.

7. The device of claim 5, wherein the plurality of packets contain different types of solid agent such that the delivery assembly can deliver different types of therapeutic agent.

8. The device of claim 2, wherein the agent delivery assembly is configured to deliver multiple doses of a therapeutic agent solution formed by the solid therapeutic agent and the liquid solvent.

9. The device of claim 1, wherein the agent delivery dispenser is configured for placement in the pericardial space.

10. The device of claim 9, wherein the agent delivery dispenser is further configured for fixation to the target tissue.

11. The device of claim 1, wherein the at least one implantable sensor comprises one or more electrodes configured to sense a potential at an implanted location within the patient.

12. The device of claim 1, wherein the agent comprises a thrombolitic agent and wherein the condition comprises myocardial ischemia.

13. The device of claim 1, wherein the controller evaluates the at least one physiologic characteristic for predictive indications of the condition and, upon detection of such predictive indications, induces the therapeutic agent delivery assembly to deliver the agent before symptomatic manifestation of the condition.

14. The device of claim 1, further comprising:
   an implantable pulse generator; and
   at least one stimulation electrode on the lead and operatively associated with the pulse generator;
   wherein the controller is further configured to monitor a cardiac activity of the patient for indications of cardiac arrhythmia and, upon detection of cardiac activity indicating cardiac arrhythmia, inducing the pulse generator and the at least one stimulation electrode to deliver therapeutic electrical stimulation.

15. An implantable patient lead comprising:
   a lead body having a distal end region configured for placement in a pericardial space;
   a connector at a proximal end of the lead body adapted for connection to an implantable therapy device;
   an implantable therapeutic agent delivery assembly entirely on the distal end region of the lead body, the delivery assembly including a structure for holding a therapeutic agent for subsequent delivery, an agent delivery dispenser coupled to the structure by a conduit and configured to deliver the agent to a target tissue, and a pressure source configured to provide pressure to the structure to induce flow of the agent from the structure to the agent delivery dispenser, wherein the delivery assembly is configured for placement in the pericardial space and the agent is entirely contained within the structure that is entirely on the lead; and
   one or more contacts on the connector, the one or more contacts in electrical contact with the therapeutic agent delivery assembly.

16. The lead of claim 15, further comprising at least one physiologic sensor on the distal end region of the lead body.

17. The lead of claim 16, wherein the at least one physiologic sensor is configured for placement in the pericardial space.

18. The lead of claim 16, wherein the at least one physiologic sensor is an electrode adapted to sense electrical potentials.

19. The lead of claim 15, wherein the structure for holding the therapeutic agent comprises an agent solvent reservoir configured to hold a liquid solvent, and a solid agent packet coupled to the reservoir by a second conduit and configured to hold a solid therapeutic agent, wherein the agent delivery dispenser is coupled to the solid agent packet.

20. The lead of claim 15, wherein the agent delivery dispenser is configured for placement in the pericardial space and is further configured for fixation to the target tissue.

21. The lead of claim 20, wherein the agent delivery dispenser comprises one or more of a micro-needle array, a barb having an internal passage for delivery of the agent, and a helix having an internal passage for delivery of the agent.

22. The lead of claim 15, further comprising at least one stimulation electrode on the distal end region of the lead body and configured for placement in the pericardial space and configured such that electrical stimulations generated by a separable implantable therapy device can be delivered via the lead to the target tissue.

* * * * *